(12) United States Patent
Bendale

(10) Patent No.: US 7,977,382 B2
(45) Date of Patent: Jul. 12, 2011

(54) THERAPEUTIC BIO PLATINUM COMPLEX

(76) Inventor: Yogesh N. Bendale, Pune (IN)

( * ) Notice: Subject to any disclaimer, the term of this patent is extended or adjusted under 35 U.S.C. 154(b) by 472 days.

(21) Appl. No.: 12/076,005

(22) Filed: Mar. 12, 2008

(65) Prior Publication Data

US 2009/0041853 A1  Feb. 12, 2009

(30) Foreign Application Priority Data

Aug. 23, 2006 (WO) .................. PCT/IB2006/052916

(51) Int. Cl.
*A61K 31/28* (2006.01)

(52) U.S. Cl. ...................................... 514/492

(58) Field of Classification Search ................... 514/492
See application file for complete search history.

(56) References Cited

U.S. PATENT DOCUMENTS

| 2002/0136660 A1* | 9/2002 | Shoji et al. | 419/19 |
| 2005/0208136 A1* | 9/2005 | Maeda et al. | 424/486 |
| 2008/0311640 A1* | 12/2008 | Cox et al. | 435/168 |

* cited by examiner

*Primary Examiner* — Raymond J Henley, III
(74) *Attorney, Agent, or Firm* — Alfred F. Hoyte, Jr.

(57) ABSTRACT

A novel bio platinum complex which increases the therapeutic applicability and effectiveness of platinum used as a cancer treatment in humans and animals especially in anti tumor treatments and to prevent the spread of cancer without fear of high toxicity. The present invention provides for a new method of administration of the bio platinum complex, which is oral administration in specific dosage with suitable carriers either by itself or in combination with other metals or minerals. The administration of the novel bio platinum complex can be carried out in combination with other plant materials depending on the nature of the treatment afforded. Use of the novel bio Platinum complex extends to agriculture and horticulture. Further, the invention is characterized by the irreversible nature of the bio platinum to its metallic form, high solubility, and the non-toxic nature when used in specific dosage, which increases the utility of platinum, in various other fields apart from its therapeutic applications. The present invention also provides for a new process for the preparation of bio platinum with the aid of plant materials.

11 Claims, 1 Drawing Sheet

THERAPEUTIC BIO PLATINUM COMPLEX

CROSS REFERENCE TO RELATED APPLICATIONS

This application claims priority of PCT application number PCT/IB2006/052916, filed Aug. 23, 2006.

BACKGROUND OF THE INVENTION

1. Field of the Invention

The present invention relates generally to therapeutic compounds for treatment of tumors. More specifically, the invention relates to a method for preparing a bio platinum compound for treating cancerous and non cancerous tumors, as well as preventing the spread (metastasis) of cancer cells in humans and animals.

2. Discussion of the Prior Art

Platinum based drugs are generally coordination complexes with desirable placement in square planar sites. However, success of Platinum based drug ranges between an upper concentration level approaching the toxicity limit where there is a high probability of success, and a lower concentration level where it falls below the minimum required for effective treatment.

Two Platinum complex agents that are widely used in clinical oncology practice are Cisplatin and Carboplatin. Cisplatin is known to cause severe renal tubular damage, reduced glomerular filtration and requires concurrent saline hydration and mannitol diuresis to eliminate any lethal or other potential damage to the kidney. Peripheral neurotoxicity is the most dose limiting factor associated with Cisplatin. Carboplatin on the other hand is known to cause severe nausea and vomiting. Although Carboplatin is relatively free from peripheral neurotoxicity, hematological toxicity where thrombocytopenia, more than leukopenia, becomes a dose limiting factor in anti-tumor treatment.

The existing platinum based anti tumor drugs are generally intravenous injectables, which are administered once in 21 days in combination with chemotherapy. When such platinum drugs are injected intravenously it results in instantaneous rise of the drug concentration level in the body. For such intravenous drugs to be of optimum utility the dosage administered has to be high which subjects the toxicity level to increase. To prevent the toxicity level from rising to the highest limit if a lower dosage is administered, the therapeutic effect of the drug is minimal. Injection leads to quick or instantaneous therapeutic effect, which will be necessary during epidemics but it is coupled with high risk of toxicity.

Moreover, the therapeutic effect of the existing platinum based drugs being intravenous injectables becomes minimal within 4-12 hours of the administration. Currently, there are very few platinum based anti-tumor drugs, which provide optimum therapeutic effect with lower toxicity level but these are injectable drugs and not ingestible. Hence it was essential to invent a therapeutically effective ingestible bio platinum, which would be non toxic or show a minimal level of toxicity.

Orally administrable platinum complexes for anti tumor treatment have been discussed in WO/1999/033782, which does not form prior art in respect of the present invention, as the new process for obtaining the novel bio platinum is completely devoid of any chemical treatment of Platinum metal and also vary in its characteristics and physical properties.

SUMMARY OF THE INVENTION

The present invention, a novel bio platinum complex, increases the therapeutic applicability and effectiveness of platinum used as a cancer treatment in humans and animals especially in anti tumor treatments and to prevent the spread of cancer without fear of high toxicity. The present invention provides for a new method of administration of the bio platinum complex, which is oral administration in specific dosage with suitable carriers either by itself or in combination with other metals or minerals. The administration of the novel bio platinum complex can be carried out in combination with other plant materials depending on the nature of the treatment afforded. Use of the novel bio Platinum complex extends to agriculture and horticulture. Further, the invention is characterized by the irreversible nature of the bio platinum to its metallic form, high solubility, and the non-toxic nature when used in specific dosage, which increases the utility of platinum, in various other fields apart from its therapeutic applications. The present invention also provides for a new process for the preparation of bio platinum with the aid of plant materials.

The object of the present invention is to increase the applicability of platinum in various fields including, but not limited to, therapeutic and to enhance the bio-availability and therapeutic applicability of platinum in anti-tumor treatment without fear of a high toxicity level, which is highly soluble and orally administrable. The novel bio Platinum complex also can be used for the treatment of plants and in agriculture as well as horticulture.

Accordingly, it is a principal object of the invention to provide an improved bio platinum complex.

It is an object of the invention to provide a method for producing an improved bio platinum complex.

The novel process is carried out in different phases which is briefly described as follows:

Phase I involves bio purification of the fine platinum metal. Fine platinum metal available in its purest form is used in phase I of the process. Phase II involves particle size reduction of the Phase I purified platinum metal. Phase III involves conversion of the phase II product into non toxic bio platinum of high therapeutic value. Each of these phases are carried out at different temperatures and with the aid of plant materials.

The standard method of administration of known platinum based drugs in humans and animals is intravenous injection. There are a few injectable platinum drugs but this does not in any manner form prior art as the present invention is not chemically obtained and is obtained with trituration of the platinum metal with plant materials. The present invention aids injectable administration of bio Platinum in specific dosage with honey, water or any other suitable carrier, which is a novel method of administration. The bio platinum can also be administered in combination with other metals or minerals or in combination with other metals and minerals in specific dosage for the treatment of humans and animals. The present invention is more cost effective in terms of therapeutic application of platinum based drugs.

These and other objects of the present invention will become readily apparent upon further review of the following specification and drawings.

BRIEF DESCRIPTION OF THE DRAWING

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION

Figure 1:
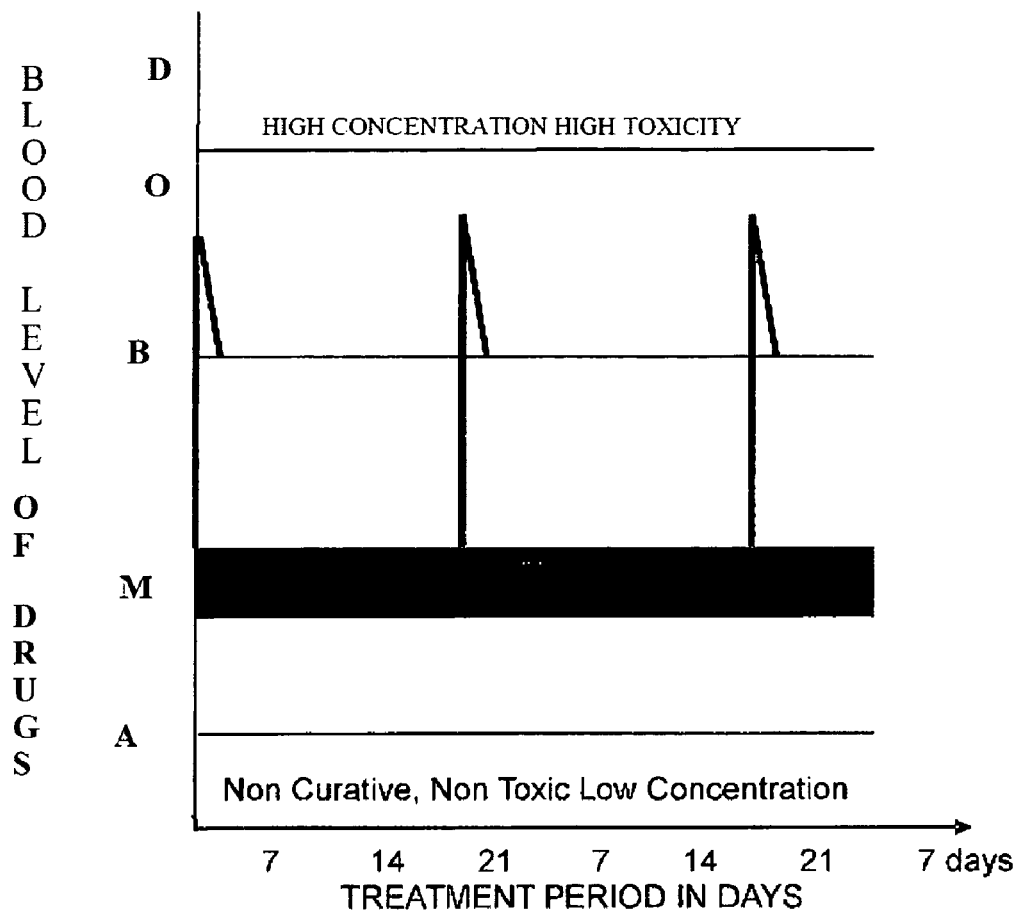
FIG. 1 shows a comparative study of a known injectable anti tumor platinum based drug and the novel bio platinum complex of the invention.

The present invention also provides for a novel process for the preparation of a bio platinum complex with the aid of plant materials. The novel process renders the platinum irreversible to its metallic state, highly soluble, and non-toxic when administered in specific dosage, which broadens the scope of utility of platinum metal in various fields apart from treatment of diseases in humans, animals and plants. The bio platinum complex obtained from the process can be used in agriculture and horticulture and is non allergenic. This present invention has high therapeutic applicability in the treatment of humans and animals especially anti tumor treatment and the prevention of spread of cancer.

The process is carried out in three phases. The plant materials used in the process include, but are not limited to, *Dolichos biflorous* and *Ocimum sanctum*. The other ingredients used in the process are mineral halite (Sodium Chloride) and Cow's urine. *Dolichos biflorous* is commonly found in India and is generally known as 'Kullathd. The process can also be carried out with the aid of other plant materials such as *Euphorbia nerifolia* (Snoohi'), *Sesbania grandiflora* (Agustyam'), *Piper betle* ('NagavalW), *Calospropris proceraf* (Arkapatarani), *Asteracanpha longifolia* ('Kokilakshd). These plant materials are also commonly found in India. Other similar plant material, known or obvious to people skilled in the art that are similar in nature to the aforementioned plant materials, would bring about similar results on being used in the process is anticipated.

Phase I of the process involves the bio purification of the pure platinum metal.

Platinum metal of high purity is heated at about 600° C. temperature until red hot (about 200 to 300° C. The red hot pure platinum metal is then boiled with cow's urine for several hours followed by the resultant product being boiled in decoction of *Dolichos biflorus* (Kullattha) for several hours. Optimum result would be obtained if the boiling of the platinum metal with both cow's urine and *Dolchos biflorous* is carried out for a minimum of 7 hours, respectively. However, the time of 7 hours cannot be considered as limiting, as the time that the boiling requires to produce optimum result varies according to quantity of the platinum metal used and the concentration of the other constituents of the process as can be determined by trial and error. The resultant product, metallic powder in nature, is again put through the process of heating and boiling with cows urine followed by *Dolichos biflorous* as described above. The process is repeated several times so as to biologically purify the platinum metal.

Phase II involves particle size reduction of the biologically purified platinum metal obtained by Phase I. The product of Phase I is converted into granular state by repeatedly triturating the biologically purified Platinum metal with the juice of *Ocimum sanctum* at temperature ranging from 22° C. to 45° C. until dry. The temperature range cannot be considered as limiting as the temperature would vary upon the speed of the trituration and the quantity of the product of Phase I. The dry product obtained from triturating the biologically purified platinum metal with *Ocimum sanctum* is then exposed to high temperature. Generally, the minimum temperature for optimum result would be in the range of 450° C.-550° C. However, the temperature range cannot be considered as limiting. After exposing the dry product obtained after trituration to high temperature as described, the temperature is gradually reduced to standard room temperature. Biomass, generally cow dung, is used as fuel for the purpose of heating so as to obtain optimum temperature and also to ensure that the temperature gradually reduces to room temperature in time after the fuel has burned out. Any fuel or method of heating could be used in place of cow dung if the fuel or method of heating would result in the same heating effect. For best results, the process of Phase II is carried out several times during when the metal gradually pulverizes, darkens and finally reduces to an extremely fine-grained dust.

Phase III involves conversion of the phase II product into bio platinum categorized by high therapeutic value, orally administrable, non-toxic when administered in specific dosage and highly soluble in nature. The product obtained from Phase II is triturated with aqueous solution of mineral halites (NaCl) at room temperature until dry. For best results this process is repeated several times i.e., the dry product obtained from the process of trituration with aqueous solution of mineral halites is further triturated with aqueous solution of mineral halites until dry. This dry product is further dried and pulverized at room temperature to obtain bio platinum in its ultra fine form, highly soluble, highly therapeutically effective and non-toxic when administered in specific dosage and also characterized by the irreversible nature of bio platinum into the metallic state of platinum.

Biomass, preferably cow dung, is used for the purpose of heating during all three phases so that the temperature gradually increases to optimum temperature and after the fuel is burned out, the temperature would gradually reduce to standard room temperature. Any fuel or method of heating could be used in place of cow dung if the fuel or method of heating would result in the same heating effect.

The present invention also provides for a novel method of administration of platinum for the treatment of diseases in humans and animals. The method involves oral administration of the novel bio platinum in therapeutically effective specific dosage. The administration can be carried out with any suitable carrier and also in combination with other metals or minerals or in combination with other metals and minerals, respectively, in specific dosage. The novel bio platinum when administered orally for anti-cancer treatment, therapeutic effect is much higher compared to the existent ingestible or injectable platinum based drugs. The toxicity level of the bio platinum is practically nil when administered in specific dosage. The method of administration of the novel bio platinum also include any other therapeutically effective route of administration including but not limited to intravenous administration.

The administrable dosage of the novel bio platinum normally ranges between 1 mg to 100 mg per day. Dosage would vary depending on various factors hence the dosage form specified as 1 mg to 100 mg cannot be considered limiting. Honey and water are the most commonly used suitable carriers but it shall not be considered as limiting as any other suitable carrier may be used for administration. Specific dosage of the other metals and minerals, which can be administered in combination with the novel bio platinum would normally range between 1 mg to 120 mg. The administrable dosage of the bio platinum and the other metals, minerals and plant materials vary on various factors, for instance the general health condition of the patient, age of the patient and in case of tumor, the kind of tumor and stage of the tumor. Hence the specified dosage cannot be considered as limiting in any manner.

The pharmaceutical composition or dosage form of the novel bio platinum for administration can be in powder form, tablet, effervescent, fluid, gelatinous, granules or in any other palatable and administrable form.

A standard man weighing 70 kg will have 5000 ml to 7000 ml blood. Half life of diffusion in 5000 ml to 7000 ml blood is 6 hours and the local concentration is an important parameter with regard to the diffusion lifetime. In case of intravenous injectable platinum based known drugs, the blood level of the drug may reach and remain at toxicity level which in turn results in comparable half life value of excretion in terms of the absorption of used or unused left over drug by kidney.

The new method of administration, ingestion of bio platinum complex, in specific daily dose, is apt for long term treatments as it provides slow constant level administration, slow constant level solubilization, slow constant level absorption, lower risk value, higher therapeutically effective period, reasonable excretion rate.

EXAMPLE

Comparative study was conducted of therapeutic effect of a known anti tumor platinum injectable drugs and the therapeutic effect of the present invention, which is represented in FIG. 1.

The one-dose cycle of an injectable drug is 21 days as shown in FIG. 1. Parenteral administration of the known anti tumor platinum drug causes an instantaneous rise in drug concentration level in the blood nearly reaching the toxicity limit and the drug concentration start tapering in 4 to 12 hours. Hence the therapeutic effective period is very limited.

The decisive factors in respect of therapeutic effect of a drug depend on the blood level (1C) and effective therapeutic life of a drug (1T'). The effective therapeutic life of drug (T) is the difference between the injection time (T) or ingestion time (T) and the d ic is excretion time (T). The blood level values C (injection blood level value), C e ic is (ingestion blood level value), C (excretion blood level value) and C (difference in e d blood level value) also influence the therapeutic effect. If C is higher than required d level then higher is the toxic effect. If C d is lower than required level, the therapeutic effect will be poor. On the other hand T values will decide the retention time in blood.

Lower the value of T e higher will be the value of C e. T ic or T is, T e and T d values will define inversely the C ic or C is, C e and C d values. Since more the lingering time of drug, lowering of (T-T) or (T-T) will govern the useful life of the drug T. Higher the ic e is e d value of difference, the drug will be more therapeutically effective but high toxicity would be the consequence.

The present invention, which is administered orally in specific dosage on daily basis as illustrated in FIG. 1, does not enter blood circulatory system excessively at any given time thus prevents instantaneous rise of platinum level in blood. The daily dose is calculated on very small percentage of solubilized drug. This method of administration is repeated every day throughout the treatment period maintaining the drug level in blood at fairly constant level.

On oral administration of the novel bio platinum complex, the absorption in blood is slow thereby maintaining constant level in blood achieving therapeutic effectiveness and lowest level of toxicity at any given instance. A very small percentage of the novel bio Platinum is absorbed through the gastrointestinal membrane. Solubilization in gastric juice in gastro intestinal tract is again a slow process extending transfer from solid to solution state very effectively.

This method of administration aids prolonged constant low-level blood concentration through out the treatment period. All stepwise processes (a) ingestion (b) solubilization ©) membrane contact and transport through membrane and (d) entry into blood stream together work in unison with desirable effects. Excretion process of left over solubilized unabsorbed platinum complex through urinary tract keeps blood platinum at desirable low level. All undissolved solid is discharged through fecal matter. Since the blood moving to kidney at any given time has a constant low level of used drug, the kidney is not under strain even for a short duration.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims:

What is claim is:
1. A process for preparation of bioplatinum, comprising:
   (a) Subjecting pure platinum metal to heat until red hot;
   (b) Dipping the red hot platinum metal in cow's urine and then subjecting it to heat until red hot;
   (c) Dipping the red hot platinum metal in decoction of *Dolichos Biflorous* and then subjecting it to heat until red hot;
   (d) Triturating the platinum complex obtained after subjecting the platinum metal to step (c) with juice of *Ocimum Sanctum* until dry and then subjecting the product obtained by the trituration to heat by use of heating method that heats the dry powder obtained by trituration gradually to high temperature and upon attaining optimum temperature gradually reduces the heat to standard room temperature;
   (e) Triturating the product of the process described in step (d) with aqueous solution of mineral halites at room temperature until dry;
   (f) Drying and pulverizing the product of the process described in step (e).

2. The process of claim 1 wherein any plant extract, including *Dolichos Biflorous, Ocimum Sanctum, Euphorbia Nerifollia, Sesbania Grandiflora, Piper Betle, Calopropris Procera, Asteracanpha Longifolia*, is used in steps (c) and (d).

3. The process of claim 1 including the step of combining the product of process step (f) with a carrier.

4. The process of claim 3 where the carrier is honey.

5. The process of claim 3 wherein said carrier is granulated and said combination is in tablet form.

6. The process of claim 3 wherein said carrier is granulated and said combination is in capsule form.

7. The process of claim 3 wherein said carrier is liquid.

8. The process of claim 3 wherein said carrier is water.

9. A method for preparing low toxicity bio platinum for use in both topically applied and internally ingested medications comprising the steps of:
   purification of a quantity of pure platinum by applying heat and a first plant extract to produce a quantity of purified platinum;
   granulating said purified platinum by triturating with a second plant extract to produce granulated bio purified platinum; and,
   triturating said granulated bio purified platinum with an aqueous solution of mineral halites until dry.

10. The method of claim 9 wherein said first plant extract is *Dolichos Biflorous*.

11. The method of claim 9 wherein said second plant extract is *Ocimum Sanctum*.

* * * * *